United States Patent

Dransch, deceased et al.

[11] 3,985,762
[45] Oct. 12, 1976

[54] PROCESS FOR THE MANUFACTURE OF 2-ALKYLSULFINYL-6-NITROBENZ-THIAZOLES

[75] Inventors: Günter Karl Wilhelm Otto Dransch, deceased, late of Eschborn, Taunus, Germany; by Annelise Klara Helene Wiesenhütter, heiress, Eschborn, Taunus, Germany; by Johanna Mathilde Flersheim, heiress, Berlin, Germany

[73] Assignee: Hoechst Aktiengesellschaft, Frankfurt am Main, Germany

[22] Filed: Jan. 2, 1975

[21] Appl. No.: 538,162

[30] Foreign Application Priority Data
Jan. 5, 1974 Germany............................ 2400419

[52] U.S. Cl. .............................................. 260/306
[51] Int. Cl.² ...................................... C07D 277/74
[58] Field of Search ................................... 260/306

*Primary Examiner*—Richard J. Gallagher
*Attorney, Agent, or Firm*—Curtis, Morris & Safford

[57] ABSTRACT

2-Alkylsulfinyl-6-nitrobenzthiazoles of the formula

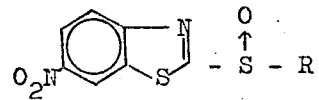

in which R is alkyl having from 1 to 10 carbon atoms are prepared by reacting 2-alkylmercaptobenz-thiazoles of the formula

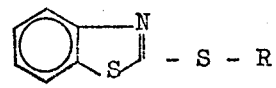

with at least 2 moles of fuming nitric acid in at least 300 grams of sulfuric acid, of at least 90 % strength, per mole of benzthiazole.

3 Claims, No Drawings

PROCESS FOR THE MANUFACTURE OF 2-ALKYLSULFINYL-6-NITROBENZ-THIAZOLES

This invention relates to a process for the manufacture of 2-alkylsulfinyl-6-nitrobenzthiazoles.

It is known to prepare 2-methylsulfinyl-6-nitrobenzthiazole by methylation of 2-mercapto-6-nitrobenzthiazole with subsequent oxidation of the thioether with peroxybenzoic acid (cf. U.S. Pat. No. 3,629,427). In this process considerable amounts of 2-methylsulfonyl-6-nitrobenzthiazole and unreacted 2-methylmercapto-6-nitrobenzthiazole are formed in addition to 2-methylsulfinyl-6-nitrobenzthiazole. This process is therefore not suitable on an industrial scale.

It is also known to prepare sulfoxides by oxidation of thioethers with nitric acid, for example by adding the sulfide to cold nitric acid (cf. Houben-Weyl "Methoden der org. Chemie" volume IX, page 214 (1955)) or by carrying out the reaction in glacial acetic acid as reaction medium (Monatshefte 31, page 695 (1910)). If, however, these methods are applied to 2-alkylmercaptobenzthiazoles, the oxidation does not take place at the sulfur atom. Instead, 2-alkylmercapto-6-nitrobenzthiazoles are obtained (cf. Chem.Soc. 1674 (1936)).

A temperature increase in this reaction to 30°–80° C leads to the formation of decomposition products.

The present invention provides a process for the manufacture of 2-alkylsulfinyl-6-nitrobenzthiazoles of the formula I

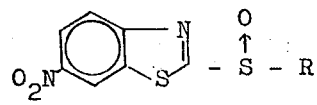

in which R represents a straight chain or branched alkyl group having from 1 to 10 carbon atoms, preferably from 1 to 6 carbon atoms, which comprises reacting, at a temperature of 0° to 45° C, 2-alkylmercaptobenzthiazoles of the formula II

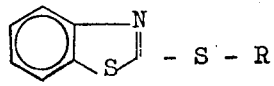

with at least twice the molar amount of fuming nitric acid in at least 300 grams of sulfuric acid of at least 90 % strength per mole benzthiazole.

Suitable radicals R are, besides those specified in the examples, for example isopropyl, secondary butyl, isobutyl, tertiary butyl, n-pentyl, n-heptyl, n-octyl, and n-decyl. Technical fuming nitric acid is generally of 98 % strength.

The sulfuric acid is used in an amount of 300, preferably 500 to about 1,800 grams, per mole of benzthiazole of formula II. It is to be noted that excess sulfuric acid, i.e. more than indicated by the upper limit of the preferred range, does not prevent the reaction from proceeding; it merely makes the process less economical as it does not improve the yield. The sulfuric acid used shall be at least 90 %, more preferably at least 93 % and particularly at least 95 % $H_2SO_4$, during the course of the entire reaction, including the water present in or formed during the reaction but not considering the nitric acid present.

In a preferred embodiment of the reaction, the 2-alkylmercaptobenzthiazole of formula II is introduced slowly into a cooled mixture of sulfuric acid and fuming nitric acid. In another preferred embodiment, the 2-alkylmercaptobenzthiazole is dissolved in part of the sulfuric acid, the solution is cooled, mixed with a mixture of the other part of sulfuric acid with nitric acid and further stirred at moderately elevated temperature. The rate of addition substantially depends on the internal temperature and, hence, on the external cooling.

Another modification of the process according to the invention consists of nitrating in a first stage the 2-alkylmercaptobenzthiazole with an excess of fuming or concentrated (63 %) nitric acid. In the former case it is advantageous to add simultaneously an excess of concentrated sulfuric acid, while in the second case this is indispensable. With fuming nitric acid the reaction is preferably carried out at 0°–5° C while cooling with ice, whereas temperatures up to 50° C are used for the reaction with concentrated nitric acid. In a second stage the alkylmercapto-n-nitrobenzthiazole obtained is then oxidized with fuming nitric acid plus concentrated sulfuric acid at a temperature below 45° C while maintaining the other reaction conditions.

The reaction time depends on the temperature and can be varied within wide limits, but is should not exceed 4 hours at a temperature of 0° to 5° C or 2 hours above room temperature, since otherwise the sulfinyl group would be split off again with oxidation. The stirring time, i.e. the period of stirring after mixing of the reaction components, is generally 1 to 7 hours.

For each mole of 2-alkylmercaptobenzthiazole at least 2 moles and preferably 2.5 to 4 moles and more of nitric acid are used. An excess of sulfuric acid and/or nitric acid above the indicated amounts is possible, but it does not improve the yield. The acids used should be as highly concentrated as possible in order to maintain the low water content of the sulfuric acid or the mixed acids.

For working up, the reaction mixture is poured into icewater, the reaction product is filtered off, washed until neutral and dried.

The reaction products are valuable fungicides and bactericides.

The following examples illustrate the invention.

EXAMPLE 1

2-Ethylsulfinyl-6-nitrobenzthiazole

At a temperature not exceeding 40° C, 195 grams (1 mole) of 2-ethylmercaptobenzthiazole were added dropwise, while stirring and cooling, to a mixture of 250 grams of fuming nitric acid of 98 % strength and 1,100 grams of concentrated sulfuric acid. The reaction mixture was then stirred for 2 hours at 40° C and poured into approximately 5 liters of water while vigorously stirring. The reaction product was filtered off, washed until neutral and dried in a drying cabinet.

210 Grams (82.1 %) of 2-ethylsulfinyl-6-nitrobenzthiazole melting at 145°–149° C were obtained.

When recrystallized from dioxane the compound melted at 159°–160° C.

| $C_9H_8N_2O_3S_2$ | molecular weight 256.27 | | |
|---|---|---|---|
| | C | H | O |
| calculated | 42.19 | 3.14 | 18.73 |
| found | 41.9 | 3.2 | 18.5 |

EXAMPLE 2

2-Methylsulfinyl-6-nitrobenzthiazole

At a temperature of 0° to 15° C, a mixture of 17.6 grams of fuming nitric acid and 35 grams of concentrated sulfuric acid was added dropwise while stirring to a solution of 18.1 grams (0.1 mole) of 2-methylmercaptobenzthiazole in 70 ml of concentrated sulfuric acid. The mixture was heated to 30°–35° C and stirred for a further 3 hours at this temperature. The reaction mixture was then poured onto 200 grams of ice, the 2-methylsulfinyl-6-nitrobenzthiazole was filtered off, washed until neutral and dried. 17.5 Grams of crude product were obtained (72.4 %).

When recrystallized from ethanol the compound melted at 193° C.

| $C_8H_6N_2O_3S_2$ | molecular weight 242.28 | | | |
|---|---|---|---|---|
| | C | H | N | O |
| calculated | 39.66 | 2.50 | 11.56 | 19.81 |
| found | 39.4 | 2.7 | 11.5 | 19.7 |

EXAMPLE 3

2-Butylsulfinyl-6-nitrobenzthiazole

At 10° C a mixture of 35 grams of concentrated $H_2SO_4$ and 18 grams of fuming nitric acid was dropped into a solution of 22.4 grams (0.1 mole) of 2-butylmercaptobenzthiazole in 60 ml of concentrated sulfuric acid. The solution was then heated to 30°–35° C and stirred for 3 hours at said temperature.

The reaction mixture was worked up as described in the preceding examples. The 2-butylsulfinyl-6-nitrobenzthiazole obtained was recrystallized from ethanol. The melting point was 105° C.

| $C_{11}H_{12}N_2O_3S_2$ | molecular weight 284.35 | | | |
|---|---|---|---|---|
| | C | H | O | S |
| calculated | 46.47 | 4.25 | 16.88 | 22.55 |
| found | 46.4 | 4.0 | 17.1 | 22.3 |

In the manner described in Examples 1 to 3 the following compounds were prepared:

| | |
|---|---|
| 2-propylsulfinyl-6-nitrobenzthiazole | m.p. 131°C |
| 2-isopentylsulfinyl-6-nitrobenzthiazole | m.p. 89°C |
| 2-hexylsulfinyl-6-nitrobenzthiazole | m.p. 77°C |

What is claimed is:

1. A process for the manufacture of a 2-alkylsulfinyl-6-nitrobenzthiazole of the formula I

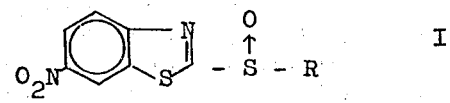

in which R is alkyl having from 1 to 6 carbon atoms, which comprises reacting, at a temperature of from 0° to 45° C, a 2-alkylmercaptobenzthiazole of the formula II

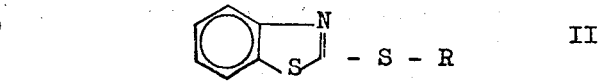

with at least 2 moles of fuming nitric acid in at least 300 grams of sulfuric acid, of at least 90 % strength, per mole of benzthiazole.

2. A process as claimed in claim 1, wherein the compound of formula II is first nitrated at about 0° to 5° C with an excess of concentrated nitric acid and sulfuric acid and the 2-alkylmercapto-6-nitrobenzthiazole obtained is then oxidized at 0°–45° C with a mixture of fuming nitric acid and concentrated sulfuric acid.

3. A process as claimed in claim 2, wherein the nitration of the compound of formula II is carried out with fuming nitric acid in the presence of concentrated sulfuric acid.

* * * * *